United States Patent
Pierre et al.

(10) Patent No.: US 12,285,285 B2
(45) Date of Patent: Apr. 29, 2025

(54) METHOD AND SYSTEM FOR REGISTRATION OF 2D OR 3D IMAGES

(71) Applicant: ECENTIAL ROBOTICS, Gieres (FR)

(72) Inventors: Arnaud Pierre, La Tronche (FR); David Armand, Saint Egreve (FR)

(73) Assignee: ECENTIAL ROBOTICS, Gieres (FR)

( * ) Notice: Subject to any disclaimer, the term of this patent is extended or adjusted under 35 U.S.C. 154(b) by 433 days.

(21) Appl. No.: 17/798,781

(22) PCT Filed: Feb. 19, 2021

(86) PCT No.: PCT/EP2021/054226
§ 371 (c)(1),
(2) Date: Aug. 10, 2022

(87) PCT Pub. No.: WO2021/165506
PCT Pub. Date: Aug. 26, 2021

(65) Prior Publication Data
US 2023/0106438 A1    Apr. 6, 2023

(30) Foreign Application Priority Data
Feb. 21, 2020 (EP) .................................... 20305170

(51) Int. Cl.
*A61B 6/00* (2024.01)
*A61B 90/00* (2016.01)
*A61B 34/20* (2016.01)

(52) U.S. Cl.
CPC ............ *A61B 6/5235* (2013.01); *A61B 90/39* (2016.02); *A61B 2034/2072* (2016.02); *A61B 2090/3966* (2016.02); *A61B 2090/3983* (2016.02)

(58) Field of Classification Search
None
See application file for complete search history.

(56) References Cited

U.S. PATENT DOCUMENTS

2016/0242724 A1* 8/2016 Lavallee ................ A61B 90/39
2022/0370152 A1* 11/2022 Lavallee ............. A61B 6/4085

FOREIGN PATENT DOCUMENTS

| EP | 2676627 A2 | 12/2013 |
|---|---|---|
| EP | 2676627 A3 | 5/2014 |

(Continued)

OTHER PUBLICATIONS

International Search Report in related PCT Application No. PCT/EP2021/054226, mailed May 27, 2021.
(Continued)

*Primary Examiner* — Leon Flores
(74) *Attorney, Agent, or Firm* — Thomas | Horstemeyer, LLP

(57) ABSTRACT

The present invention relates to a method for registration of 2D images of a region of interest of a patient, wherein the images are acquired using an X-ray imaging system and an imaging kit (1) comprising abase (2) and a registration phantom (3), wherein the method comprises the following steps: receiving a first (respectively second) set of 2D X-ray images of at least one first (respectively second) portion of a region of interest, said first and second sets of images comprising each at least two 2D images containing each at least one detectable radiopaque fiducial of the registration phantom (3); registering the first (respectively second) set of images in the coordinate system of the registration phantom in the first (respectively second) phantom fixation position; registering the first and second sets of 2D images in the coordinate system of the base.

26 Claims, 14 Drawing Sheets

(56) References Cited

FOREIGN PATENT DOCUMENTS

| EP | 2868277 A1 | 5/2015 |
| EP | 3361977 A1 | 8/2018 |
| WO | 2017064254 A1 | 4/2017 |

OTHER PUBLICATIONS

European Search Report in related European Application No. EP 20305170, mailed Jul. 28, 2020.

\* cited by examiner

METHOD AND SYSTEM FOR REGISTRATION OF 2D OR 3D IMAGES

CROSS REFERENCE TO RELATED APPLICATIONS

This application is the 35 U.S.C. § 371 national stage application of PCT Application No. PCT/EP2021/054226, filed Feb. 19, 2021, which application claims the benefit of European Application No. EP 20305170.1 filed Feb. 21, 2020, both of which are hereby incorporated by reference herein in their entireties.

FIELD OF INVENTION

The present invention relates to medical imaging, notably to methods and systems for registering 2D images or 3D images acquired with an X-ray imaging system.

BACKGROUND OF INVENTION

During orthopedic and trauma surgery, fluoroscopy-based navigation system allows the tracking of surgical instruments and the superposition of their contour onto fluoroscopy images in real time. In view of carrying out fluoro-navigation, the instruments used during the surgical intervention are equipped with a tracker coupled to a localization system. Another tracker is mounted onto the patient and is also seen by the localization system. This enables the surgeon to know precisely the position of the surgical instruments at any time of the procedure without need to take additional X-ray image. Distortion of the fluoro-images is common and is notably caused by the flexibility of the C-arm and the interference with the other equipment in the operation room. The distortion is thus corrected by registering the X-ray imaging using as reference radiopaque markers rigidly positioned on the patient.

Furthermore, orthopedic and trauma surgery often need for imaging of large areas of a human body, such as the adult spine. However, standard imaging devices usually configured to perform fluoro-navigation are generally limited to a relatively small region of interest.

Nowadays, such large-scale images are often generated by stitching together multiple small images of the wide zone to be imaged. The alignment of neighboring images with each other is generally performed by identifying common anatomic features in a pair of neighboring images, and mutually aligning the neighboring images laterally and angularly until those identified features are commonly located in the final stitched composite large-scale image.

However, the known stitching methods can be problematic since the matching of features in adjacent images is complicated by inevitable image distortions which arise from cone-beam X-ray imaging techniques. Furthermore, the generation of a series of images using a complex path of the C-arm, leads to a series of image frames having orientations and positions which do not generally have defined relations with each other.

In this context arises the need for an imaging kit and a method able to use fluoroscopic images of a limited area of the subject to reconstruct large scale images with a higher accuracy and clarity of reproduction of the patient's features than the ones of the currently available stitching methods.

SUMMARY

An imaging kit for registering 2D images or 3D images acquired with an X-ray imaging system is used, said imaging kit comprising:

a base, made of a substantially radiotransparent material, said base being configured to be rigidly secured to a patient's bone over a first region of a patient's body;

at least one registration phantom having a fiducials support of substantially radiotransparent material comprising a plurality of radiopaque fiducials;

the base comprising at least one base fixation element and the at least one registration phantom comprising at least one phantom fixation element for reproducibly attaching the registration phantom to the base;

wherein the at least one registration phantom comprises at least one elongated member bearing the phantom fixation element and extending from the fiducials support, the elongated member and the base fixation element and phantom fixation elements being configured so as to provide at least one fixation position where the fiducials support is spaced apart from the base such that the fiducials support extends over a second region of the patient's body distant from the first region. The elongated member, the at least one base fixation element and the at least one phantom fixation element may be configured so as to provide at least two distinct fixation positions relative to the base.

The imaging kit advantageously allows to position the registration phantom in the center of a region of interest to be acquired by the x-ray imaging system (i.e. surgical field), while fixing the base on a body part of the patient in proximity of said region of interest. Advantageously, since the base does not need to be fixed inside the surgical field, the surgeon will have a clear surgical site allowing him to perform a greater variability of acts. Furthermore, the invention advantageously allows to fix the base on a more easily accessible anatomic part of the patient.

According to one embodiment, the imaging kit further comprises a tracker comprising a tracker fixation element configured to reproducibly rigidly attach the tracker to the base, wherein the base fixation element is configured to reproducibly interchangeably attach the tracker and the registration phantom. The imaging kit comprising the tracker may be used for fluoro-navigation. Advantageously when the tracker is fixed to the base positioned outside or in the periphery of the surgical field, it will be as well positioned outside the region of interest so as to hinder as less as possible the surgeon.

According to one embodiment, the fiducials in the fiducials support are disposed on a curved surface having a predefined curvature radius.

According to one embodiment, the elongated member extends from the fiducials support along a longitudinal axis and 3D position of the plurality of radiopaque fiducials is known in a coordinate system of said registration phantom.

According to one embodiment, the imaging kit further comprises in the fiducials support a proximal and a distal fiducial with regard to the elongated member, wherein the longitudinal dimension of the elongated member is a multiple of the maximal distance between the projections of the distal and proximal fiducial on the longitudinal axis.

According to one embodiment, the phantom fixation element of the elongated member is further configured to be attached to a second registration phantom while being reproducibly attached to the base.

According to one embodiment, the imaging kit comprises at least two registration phantoms wherein the first registration phantom and the second registration phantom comprise cooperating fixation elements configured to attach the first registration phantom to the second registration phantom while being reproducibly fixed to the base.

According to one embodiment, the elongated member comprises at least two elements serially movably connected to each other. In this embodiment the 3D position of the plurality of radiopaque fiducials is known in the coordinate system of the fiducials support but not known in the coordinate system of the base.

According to one embodiment, the base fixation element and phantom fixation element comprise complementary magnetic elements configured to maintain the base and the registration phantom attached to each other.

An object of the invention is a system comprising an X-ray imaging system, the imaging kit and a control unit configured to perform the following steps in order to register 2D images of at least one region of interest of a patient:

receive at least one first set of 2D X-ray images of at least one first portion of the region of interest acquired by the X-ray imaging system and the imaging kit with the at least one base fixation element and the at least one phantom fixation element in a first fixation position corresponding to a first phantom fixation position, wherein said first set of images comprises at least two 2D images containing each at least one detectable radiopaque fiducial of the registration phantom;

receive at least one second set of 2D X-ray images of at least one second portion of the region of interest acquired by the X-ray imaging system and the imaging kit with the at least one base fixation element and the at least one phantom fixation element in a second fixation position corresponding to a second phantom fixation position, wherein said second set of images comprises at least two 2D images containing each at least one detectable radiopaque fiducial of the registration phantom;

register the first set of images in the coordinate system of the registration phantom in the first phantom fixation position and second set of images in the coordinate system of the registration phantom in the second phantom fixation position;

register the first and second sets of 2D images in the coordinate system of the base using known positions of the fiducials support in a coordinate system of the base for the first and second phantom fixation positions.

According to one embodiment, the base is configured to be rigidly fixed on a vertebra of the patient, notably on the spinous process of the vertebra.

According to an alternative embodiment, the base is configured to be rigidly fixed on the femur and at least one registration phantom is configured to have its fiducials support extending over the kneecap when the registration phantom is attached to the base. Additionally, at least a second registration phantom may be configured to have its fiducials support extending over the neck of the femur when the registration phantom is attached to the base fixed on the femur.

In an alternative embodiment, the base is configured to be rigidly fixed on the tibia and at least one registration phantom is configured to have its fiducials support extending over the calcaneus when the registration phantom is attached to the base.

According to one embodiment, the tracker is an optical tracker, an ultrasound-based tracker or an electromagnetic tracker.

The present invention further relates to a method of registration of 2D images of at least one region of interest of a patient, wherein the images are acquired using an X-ray imaging system and the imaging kit according to any one of the embodiments hereabove.

The method comprises the following steps:
a) receiving at least one first set of 2D X-ray images of at least one first portion of the region of interest and a second set of 2D X-ray images of at least one second portion of the region of interest, wherein the base is fixed on the skin or a body part of the patient and one registration phantom is attached on the base in a first fixation position during the acquisition of the first set of 2D X-ray images and one registration phantom is attached on the base in a second fixation position during the acquisition of the second set of 2D X-ray images, such that said first and second set of images comprise each at least one 2D image containing each at least one detectable radiopaque fiducial of the registration phantom; wherein the position of fiducials support in a coordinate system of the base for the first and second fixation position is known;
b) registering the first set of images in the coordinate system of the registration phantom in the first fixation position and second set of images in the coordinate system of the registration phantom in the second fixation position;
c) registering the first and second set of 2D images in the coordinate system of the base using the known position of the fiducials support in the coordinate system of the base for the first and second fixation position.

Regarding step a), the base may be fixed on the skin or a body part of the patient and a registration phantom may be attached to the base in a first phantom fixation position during the acquisition of the first set of 2D X-ray images and the registration phantom may be attached to the base in a second phantom fixation position different from the first phantom fixation position during the acquisition of the second set of 2D X-ray images, such that said first and second sets of images comprise each at least two 2D images containing each at least one detectable radiopaque fiducial of the registration phantom; wherein the position of the fiducials support in a coordinate system of the base in the first and second phantom fixation positions is known.

Step b) may comprise registering the first set of images in the coordinate system of the registration phantom in the first phantom fixation position and second set of images in the coordinate system of the registration phantom in the second phantom fixation position.

Step c) may comprise registering the first and second sets of 2D images in the coordinate system of the base using the known position of the fiducials support in the coordinate system of the base for the first and second phantom fixation positions.

Advantageously, the method of the present invention allows to obtain a unique 3D image of the first and second portion of the region of interest.

According to one embodiment, the step b) comprises for each first and second set of images:
computing an optimal rigid transformation between a coordinate system of the X-ray system and the coordinate system of the registration phantom in the first and second fixation position respectively by optimizing the registration between the known 3D position of at least one fiducial of the registration phantom and the corresponding 2D position of said fiducial detected in at least two different images;
applying said optimal rigid transformation to the 3D position of said at least one fiducial of the registration phantom in the first and second fixation position respectively to determine its respective transformed 3D position in the coordinate system of the X-ray imaging system.

The method of the present invention is a computer implemented method.

According to one embodiment, the method further comprises a step of computing at least one 3D image within the coordinate system of the base using at least a part of the first and/or second set of 2D images.

According to one embodiment, at least two 2D images of the first or second set of 2D images are used to determine the position of at least one anatomical point in the coordinate system of the base.

According to one embodiment, at least one 2D image of the first or second set of 2D images is used to determine at least one anatomical axis in the coordinate system of the base. An anatomical axis may be the vertebral axis C7 and the axis of the hip axis which a used in combination for the evaluation of scoliosis (i.e. verification of coronal equilibrium). Other examples are the axis defined in-between the shoulders and the axis in-between the hips.

According to one embodiment, the fiducials support in the first configuration is in proximity of the fiducials support in the second configuration such that the first and second portion of the region of interest in the first and second set of 2D images are at least partially overlapping; in other words, the first fixation position and the second fixation position may be chosen such that the first and second portions of the region of interest in the first and second sets of 2D images are at least partially overlapping. The method further comprises the step of registering a first and a second 3D image computed respectively from the first and second set of 2D images so as to obtain a connected 3D image of the first and second portion of the region of interest.

Another object is a method for registration of 2D images of at least one region of interest of a patient, wherein the images are acquired using an X-ray imaging system, said method comprising the following steps:

providing an imaging kit according to any one of the embodiments described hereabove;

fixing the base to the skin or to a body part of the patient in proximity of the region of interest;

mounting the registration phantom onto the base in a first fixation position using the base fixation element and phantom fixation element, wherein the position of the fiducials support in said first fixation position is known in a coordinate system of the base;

acquiring with the X-ray imaging system at least one first set of 2D images of at least one first portion of the region of interest, wherein at least one 2D images contain each at least one detectable radiopaque fiducial of the registration phantom;

mounting the registration phantom onto the base in a second fixation position using the base fixation element and phantom fixation element, wherein the position of the fiducials support said second predetermined fixation position is known in the coordinate system of the base;

acquiring with the X-ray imaging system at least one second set of 2D images of at least one second portion of the region of interest, wherein at least two 2D images contain each at least one detectable radiopaque fiducial of the registration phantom;

for each first and second set of images:
computing an optimal rigid transformation between a coordinate system of the X-ray system and the coordinate system of the registration phantom in the first and second fixation position respectively by optimizing the registration between the known 3D position of at least one fiducial of the registration phantom and the corresponding 2D position of said fiducial detected in at least two different images;

applying said optimal rigid transformation to the 3D position of said at least one fiducial of the registration phantom in the first and second fixation position respectively to determine its respective transformed 3D position in the coordinate system of the X-ray imaging system;

registering the first and second set of 2D images in the coordinate system of the base using the known position of the fiducials support in the coordinate system of the base for the first and second fixation position.

The present invention further related to a computer program comprising instructions, which when the program is executed by a computer, causes the computer to carry out the steps of the method according to any one of the embodiments described hereabove.

The present invention further related to a computer-readable storage medium comprising instructions that when executed by a computer, causes the computer to carry out the steps of the method according to any one of the embodiments described hereabove.

The present invention further related to a data processing apparatus comprising a processor configured to perform the steps of the method according to any one of the embodiments described here above.

Definitions

In the present invention, the following terms have the following meanings:

"Patient" refers to a mammal, preferably a human. In the sense of the present invention, a subject may be a patient, i.e. a person receiving medical attention, undergoing or having underwent a medical treatment, or monitored for the development of a disease.

"Fluoroscopic navigation" or "fluoro-navigation" refers to the technic of localization of the position of a surgical instrument relative to the anatomy of the patient. By superimposing the instrument's geometry onto fluoroscopic images (i.e. X-ray images), the surgeon can follow live the progression of the intervention.

"Image registration" refers to the process of transforming different sets of data into one coordinate system.

DETAILED DESCRIPTION

The invention is carried out in a context of planification of orthopedic surgery and/or a context of fluoro-navigation, in order to navigate surgical tools tracked by a localization system in an X-ray image acquired by a medical imaging system in the referential of the localization system.

This invention relates to an imaging kit for registering 2D images or 3D images acquired with an X-ray imaging system.

The X-ray imaging system comprises at least one X-ray source and at least one X-ray detector. For example, the medical imaging system can be a C-arm, an O-arm or a scanner.

A C-arm is designed to allow the source and detector to rotate along a C shaped gantry while obtaining projection images of the patient or object placed between the X-ray source and the X-ray detector of the gantry. The C-arm is capable of acquiring projection images over approximately 200° for example to be use for cone-beam computed tomography 3D image reconstruction.

The X-ray imaging system may be motorized, notably the C-shaped arm may comprise motors allowing movement horizontally, vertically and around the swivel axes, so that X-ray images of the patient are produced from almost any angle. Each motor is associated to an encoder allowing knowing, at any time, the relative position of the medical imaging system with respect to a reference position. When a 2D image is acquired, the corresponding position of the imaging system is recorded. Thus, each 2D image is recorded in the referential of the imaging system.

In general, several 2D images of the surgical site are acquired at the beginning of the surgical intervention and may be used for reconstruction of a 3D image. Besides, during the surgical intervention, one or more extra 2D or 3D images may be acquired to check progress of the intervention. Usually in order to obtain a 3D, CT-like image, the C-arm system performs a sweep around the patient, acquiring up to several hundred 2D views.

The imaging kit comprises a base made of a substantially radiotransparent material in order to be less visible as possible on the X-ray images. For substantially radiotransparent material it is meant a material having a small mass attenuation coeffect and that therefore does not quickly attenuate an X-ray beam passing through. More precisely a substantially radiotransparent material in the sense of the present invention has a mass attenuation coeffect inferior to $2.0 \cdot 10^{-1}$ cm$^2$/g for an energy of the X-ray beam comprised between 100 and 200 keV. This definition of materials comprises for example the PMMA and polyethylene.

The base is configured to be rigidly fixed to a patient's bone. By "rigidly fixed" is meant in the present text that the base does not move with respect to the bone during the surgical intervention. The fixation may be either direct, using for example at least one percutaneous pin, needle, broach or screw implanted into the bone in a minimally invasive way, or indirect by using for example attachment means external to the bone, such as an adhesive tape on the skin close to the bone, straps, etc. to immobilize the base with respect to the bone without passing through the patient's skin, or by open surgery using a clamp onto the bone (i.e. a clamp fixed on the spinous process).

According to one embodiment, the base has a support surface intended to face the bone, tissues surrounding the bone and/or the patient's skin. When the base is directly fixed to the bone, the patient's skin or tissues surrounding the bone may be located between the base and the bone. The base and the support surface may have any shape (e.g. circular, rectangular, etc.) and size suitable for the intended application, in particular depending on the shape and size of the body part to which the base has to be fixed. For example, for spine surgery, the base preferably has an elongated shape so as to be fixed to at least two or three adjacent vertebrae, whereas for shoulder surgery the base is rather circular with an oblong extension so as to be fixed to the acromion. The support surface may extend in a plane or may be either concave or convex, rigid or deformable.

Advantageously, the base may have a height of less than 20 mm so as to be very compact and only protrudes to a limited extent from the patient's skin. Thus, it is quite unlikely that the medical staff unintentionally hits the base and thus displaces it relative to the bone during the surgical intervention.

In one embodiment, the base comprises a plurality of radiopaque fiducials disposed in a known 3D position in a coordinate system of the base.

The imaging kit further comprises at least one registration phantom. The registration phantom comprises a fiducials support of substantially radiotransparent material comprising a plurality of radiopaque fiducials disposed in a known 3D position in a coordinate system of said registration phantom.

The radiopaque fiducials offer radiographic contrast relative to the fiducials support of substantially radiotransparent material and the body tissues. The radiopaque material may have a mass attenuation coeffect comprised in the range going from 1.0 cm$^2$/g to 5.5 cm$^2$/g for an energy of the X-ray beam comprised between 100 and 200 keV. The thickness of the fiducial may range from about 0.5 mm to about 10 mm and the radiopaque material may have at least one element with an atomic number of from about 22 to about 83. The fiducial may include an oxide or Salt material having at least one element with an atomic number of from about 22 to about 83. The fiducial may include barium Sulfate, bismuth trioxide, iodine, iodide, titanium oxide, Zirconium oxide, gold, platinum, Silver, tantalum, niobium, Stainless Steel, or combinations thereof. The fiducial may be coated or alloyed with a radiopaque material that has a mass attenuation coeffect comprised in the range between 1.0 cm$^2$/g and 5.5 cm$^2$/g for an energy of the X-ray beam comprised between 100 and 200 keV.

When a 2D image is acquired with the X-ray imaging system, the radiopaque fiducials are visible in the 2D image. Since the shape, size and arrangement of the radiopaque fiducials is known, the image can be located in the referential of the registration phantom and the reconstruction of the 3D image can be carried out using the position of the radiopaque fiducials in each 2D image for registration.

The radiopaque fiducials have a predetermined spatial arrangement which may be affected by a variability due to the uncertainty intrinsic to the fabrication. The exact 3D position in a coordinate system of said registration phantom of the radiopaque fiducials may be known, for example, by metrology or based on the assumption that the manufacturing process of the phantom is precise and reproducible enough to ensure that the desired position of the fiducials is obtained. Advantageously, the geometry of the phantom and the arrangement of the radiopaque fiducials are specific to the region of interest to be imaged.

Since the registration phantom is not required during the whole surgical intervention but only during images acquisition with the X-ray imaging system, the base comprises a base fixation element configured to cooperate to another fixation element comprised in the registration phantom, herein called phantom fixation element, for attaching/detaching the registration phantom to/from the base.

According to one embodiment, the base fixation element comprises at least one pin protruding from the surface of the base opposite to the support surface and the phantom fixation element comprises at least one respective complementary opening. Alternatively, the base fixation element comprises at least one opening in the surface of the base opposite to the support surface and the phantom fixation element comprises at least one respective complementary pin protruding.

According to one embodiment, the base fixation element and phantom fixation element comprise complementary magnetic elements configured to maintain the base and the registration phantom attached to each other. In this embodiment, the phantom fixation element is advantageously held in place magnetically so that if the registration phantom is accidentally hit by a member of the medical stuff it will pull out of the base without damaging the base fixation element or displacing the base from its initial fixation position on the patient's bone. Furthermore, thanks to this embodiment attachment and removal of the registration phantom and, if suitable, the tracker, can be made easily without requiring any tool. Since the cooperating fixation elements of the base and the registration phantom are configured to allow reproducible fixation of the registration phantom on the base and that the relative position of the registration phantom with respect to the base is known, the disposition of the fiducials is known also in the coordinate system of the base.

The at least one registration phantom comprises at least one elongated member extending from the fiducials support along a longitudinal axis. Said elongated member bears the phantom fixation element. The elongated member, the base fixation element and phantom fixation elements are configured so as to provide at least one fixation position where the fiducials support is spaced apart from the base so as to extend over another region of the patient's body than the region over which the base extends. This configuration allows to position the registration phantom in the center of the region of interest to be acquired by the 2D images (i.e. surgical field), while fixing the base on a body part of the patient in proximity of said the region of interest. Advantageously, if the base is not fixed inside the surgical field, the surgeon will have a clear surgical field allowing him to perform a greater variability of acts. Furthermore, in the case of fluoro-navigation, when the tracker is fixed onto the base, it will be as well positioned outside the region of interest so as to hinder as less as possible the surgeon.

According to one embodiment, the elongated member comprises at least two elements serially movably connected to each other. Each element may have an elongated shape and the connection between them may be ensured by a connection element connected to an end of the first element and an end of the second element. The connection may be a hinge connection or a swiveling connection with three degrees of freedom or alternatively a slide link.

In one embodiment, a connection element connects the elongated member to the fiducials support or one of the elements of the elongated member to the fiducials support. The connection may be a slide link, hinge connection or a swiveling connection with three degrees of freedom. These embodiments concerning an articulated elongated member advantageously allow to adapt the relative position between the base and fiducial support according to the specific anatomy of each patient so that when the registration phantom is rigidly fixed to the base the fiducial support is positioned at the center of the region of interest and as near as possible to the bone. Moreover, the articulated elongated member allows to adapt one registration phantom configuration to multiple different body parts or to patients of different sizes.

In these embodiments concerning registration phantoms with an articulated elongated member, the 3D position of the plurality of radiopaque fiducials is known in the coordinate system of the fiducials support but not known in the coordinate system of the base. It may be determined at any moment during the surgical procedure. To this end, a localization system (for example a camera) may be used to register the 3D position of the plurality of radiopaque fiducials known in the coordinate system of the fiducials support in the coordinate system of the base. For example, a registration tool equipped with a tracking apparatus may be reproducibly positioned onto both fiducials support and base, such as the localization system is able to determine the rigid transformation between said fiducials support and base in the coordinate system of said localization system. Therefore, the 3D position of the plurality of radiopaque fiducials is known in the coordinate system of the base by combining said rigid transformations.

According to one embodiment, the base fixation element and the at least one phantom fixation element may be configured to allow the positioning of the registration phantom in at least one second fixation position where the fiducials support is spaced apart from the base, said at least one second fixation position being different from the fixation position mentioned above. The base fixation element and the at least one phantom fixation element may be symmetrically placed along the longitudinal axis so that for a unique configuration of cooperating base fixation element and phantom fixation element at least two fixation positions are allowable.

The fiducials support and elongated member of the registration phantom may have any shape and size suitable for the intended application. In particular, since the registration phantom is only attached to the base when it is required for image acquisition, the fiducials support can have size close to that of the field of view of the X-ray imaging system. This advantageously allows to have the radiopaque fiducials located at a greater distance from each other and thus improve the accuracy of the registration.

According to one embodiment, the fiducials support comprises a central portion and two lateral wings extending on either side of said central portion. Preferably, the lateral wings are integral with the central portion. Depending on the application, the central portion and lateral wings may substantially extend in a plane; otherwise, the lateral wings may be sloping with respect to the central portion. In another embodiment, the wings may extend above the central portion.

According to one embodiment, the fiducials in the fiducials support are disposed on a curved surface having a predefined curvature radius. In this embodiment, the central portion and lateral wings may substantially extend in a curved surface having a predefined curvature radius. Said curvature radius is indirectly related to the design of the C-arm of the X-ray imaging system (i.e. dimensions and distance between of the X-ray source and the X-ray detector and the trajectory used by the C-arm for the acquisition), and from the shape of the anatomical are of the patient that is under acquisition (i.e. curved surface of the back or the calf). The radius of curvature of the fiducials support is configured to conform to the curvature of the reconstructed volume of the 3D image acquired from the X-ray imaging device. Advantageously, this embodiment allows to optimize the position of the 3D volume to be reconstructed.

In one embodiment, the central portion of the fiducials support bears a second phantom fixation element configured to position the registration phantom in a third fixation configuration. In this third fixation position the registration phantom is fixed to the base so that the fiducials support is positioned on top of the base. In this configuration the central portion of the fiducials support may overlap to the base.

In one embodiment, the imaging kit comprises at least two registration phantoms. The first registration phantom and the second registration phantom comprise cooperating fixation elements configured to cooperate so as to fix the first registration phantom to the second registration phantom while being reproducibly attached to the base.

Depending on the surgical site for which is designed the imaging kit, the elongated member and the fiducials support of the registration phantom may lie on two coplanar planes or on two planes forming an angle. In other words, the elongated member is tilted with respect to the fiducials support at the insertion point between the elongated member and the fiducials support. According to one embodiment, the elongated member is curved along the longitudinal direction with a predefined radius of curvature.

In one embodiment, one registration phantom comprises two fiducials supports. Both fiducials supports may have the same shape and size and be symmetrically positioned one on each end of the elongated member. Alternatively, the elongated member may comprise an elongated protrusion at the end of which is fixed the second fiducials support. The fiducials supports may as well have different shapes and dimensions to better adapt to the anatomy of the surgical field.

According to one embodiment, the fiducials support comprises a proximal and a distal fiducial with regard to the elongated member. The longitudinal dimension of the elongated member is set to be a multiple of the maximal distance between the projections of said distal and proximal fiducial on the longitudinal axis. This embodiment is particularly advantageous in the implementation of the method of registration of the present invention when the surgeon needs to access a larger image of the surgical field. Indeed, in this embodiment, when a first 3D image is reconstructed with the registration phantom in the first fixation position where the fiducials support is spaced apart from the base and a second 3D image is reconstructed with the registration phantom in the third fixation position where the fiducials support is positioned over the base, the volume acquired in the first and second 3D images are at least partially overlapping. These two 3D images may be further processed to obtain a connected larger 3D image without losing information on the anatomy of the patient. For connected volume (i.e. connected 3D image) it has to be understood a volume which is path-connected and wherein every path between two points in the volume (i.e. two voxels) can be continuously transformed into any other such path while preserving the two points in question.

According to one embodiment, the imaging kit further comprises a tracker comprising a tracker fixation element configured to reproducibly rigidly attach the tracker to the base. Said coupling between the base and the tracker may be permanent (the tracker being integral with the base or irreversibly fixed to the base) or temporary (the tracker being detachable from the base).

According to one embodiment where the tracker is detachable from the base, the fixation element of the registration phantom (i.e. phantom fixation element) is the same as for the tracker (i.e. tracker fixation element). In this way, the design of the base is as simple as possible and no space is lost by providing two distinct fixations areas on the base.

The base fixation element and tracker fixation element may be configured to allow one or more determined possible positions of the tracker with respect to the base.

According one embodiment, the tracker can be detached from the base during images acquisition so as to obtain cleaner images or when no surgical tool navigation is required so as to reduces the risk of having the tracker hit by the medical staff and thus causing a displacement of the base relative to the bone. It also saves operating space when the tracker is not needed.

In a preferred embodiment, the base fixation element of the base is configured to reproducibly interchangeably attach the tracker and the registration phantom.

According to one embodiment, the tracker is an optical tracker (either active or passive).

Alternatively, the tracker may be an electromagnetic tracker, which has the advantage of being more compact than an optical tracker. In a preferred embodiment, the electromagnetic tracker contains inertial sensors that can be used to detect the presence of artefacts.

According to one alternative embodiment, the tracker is an ultrasound-based tracker or any other tracking technology known by the skilled person.

Preferably, the tracker fixation element for tracker is the same as for the registration phantom. In this way, the design of the base is as simple as possible and no space is lost by providing two distinct fixations areas on the base.

According to one embodiment, the base and tracker fixation element comprise complementary magnetic elements configured to maintain the base and the tracker attached to each other. In this embodiment the tracker fixation element is advantageously held in place magnetically so that if the tracker is accidentally hit by a member of the medical stuff it will pull out of the base without damaging the base fixation element or displacing the fixation position of the base on the patient's bone or skin. Maintaining the base fixed to the patient in a unique position along all the intervention is crucial for allowing correct fluoro-navigation.

According to one embodiment, the base is configured to be rigidly fixed on at least one vertebra of the patient, notably on the spinous process of the vertebra.

According to one embodiment, the base is configured to be rigidly fixed on the femur and at least one registration phantom is configured to have its fiducials support extending over the kneecap when the registration phantom is attached to the base. In one embodiment, at least one second registration phantom is configured to have its fiducials support extending over the neck of the femur when the registration phantom is attached to the base fixed on the femur. The length of the elongated member of the two registration phantoms is adapted to the anatomy so that the fiducials supports are correctly positioned in the center of the field of view of the C-arm at the kneecap and the neck of the femur. According to one embodiment wherein the base is fixed on the femur, the base is configured so that the longitudinal axis of the registration phantom is positioned at approximately 45 degrees with respect to the tracker. Notably, the base may comprise two base fixation elements, one configured to rigidly fix the registration phantom and one configured to rigidly fix the tracker. The imaging kit of the present embodiment may be advantageously used during hip prosthesis implantation surgeries.

According to one embodiment, the base is configured to be rigidly fixed on the tibia and at least one registration phantom is configured to have its fiducials support extending over the calcaneus when the registration phantom is attached to the base. This kit configuration may be advantageously used in surgeries such as ankle arthrodesis or ankle distraction arthrolysis.

According to one embodiment, the base is configured to be rigidly fixed on the iliac chest or iliac spine and at least one registration phantom is configured to have its fiducials support extending over the acetabulum when the registration phantom is attached to the base.

The present invention also relates to a method for registration of 2D images of at least one region of interest of a patient, wherein the images are acquired using an X-ray imaging system and the imaging kit according to any one of the embodiments described hereabove.

According to one embodiment, the method comprises a preliminary step consisting in receiving at least one first set of 2D X-ray images of at least one first portion of the region of interest and a second set of 2D X-ray images of at least one second portion of the region of interest. The region of interest comprises the surgical field and any anatomical repair that may be useful the surgeon in the planification of the surgery.

According to one embodiment, the method also comprises the step of acquiring the first and second set of 2D images.

The first set of 2D X-ray images of at least one first portion of the region of interest are acquired with the imaging kit having the base fixed on the skin or a body part of the patient and one registration phantom attached on the base in a first fixation position. The X ray-imaging system has been positioned with respect to the imaging kit so that at least part of the fiducials support in the first fixation position is comprised in its field of view so that the first set of images acquired comprises at least two 2D images containing each at least one detectable radiopaque fiducial of the registration phantom. The second set of 2D X-ray images of at least one second portion of the region of interest are acquired with the same base (i.e. same position of the base) used for the acquisition of the first set of images and one registration phantom attached on the base in a second fixation position. The X ray-imaging system has been positioned with respect to the imaging kit so that at least part of the fiducials support in the second fixation position is comprised in its field of view so that the second set of images acquired comprises at least two 2D images containing each at least one detectable radiopaque fiducial of the registration phantom. The position of fiducials support in a coordinate system of the base for the first and second fixation position is known. Since the position of the fiducials in the registration phantom is known as well as the relative position of the fiducials support in the coordinate system of the base for the first and second fixation position is known, the position of the fiducials for the first and second fixation position in the coordinate system of the base is known.

Only one registration phantom, configured to be fixed to base in the first and the second fixation position, according to the embodiments described above, may be used for the acquisition of the first and second set of images. Alternatively, they may be used a first and second registration phantom configured to be fixed to the base respectively in a first and second fixation position.

According to one embodiment, the method of the present invention comprises the step of registering the first set of images in the coordinate system of the registration phantom in the first fixation position and the second set of images in the coordinate system of the registration phantom in the second fixation position.

This registration step may be implemented by:
  computing an optimal rigid transformation between a coordinate system of the X-ray system and the coordinate system of the registration phantom in the first and second fixation position respectively by optimizing the registration between the known 3D position of at least one fiducial of the registration phantom and the corresponding 2D position of said fiducial detected in at least two different images;
  applying said optimal rigid transformation to the 3D position of said at least one fiducial of the registration phantom in the first and second fixation position respectively to determine its respective transformed 3D position in the coordinate system of the X-ray imaging system.

According to one embodiment, the method further comprises a step of registering the first and second set of 2D images in the coordinate system of the base using the known position of the fiducials support in the coordinate system of the base for the first and second fixation position.

According to one embodiment, at least two 2D images of the first or second set of 2D images are used to determine the position of at least one anatomical point in the coordinate system of the base. This embodiment is notably implemented in the case of the surgery of the knee wherein may be used the imaging kit comprising one base configured to be fixed on the femur and two registration phantoms configured to have one fiducials support extending over the kneecap and the other extending over the neck of the femur when they are fixed on the base.

According to one embodiment, the method further comprises a step of computing at least one 3D image within the coordinate system of the base using at least a part of the first and/or second set of 2D images. In this 3D images, the first 3D volume reconstructed from the first set of 2D images and the second 3D volume (i.e. image) reconstructed from the second set of 2D images may be disjointed. For example, the first 3D volume may comprise cervical vertebras C1 and C2 while the second 3D volume may comprise the thoracic curvature vertebras T4 and T5 or the first 3D volume may comprise neck of the femur while the second 3D volume may comprise kneecap. In this embodiment, the first 3D volume and the second 3D volume do not overlap.

According to one embodiment, the method comprises a step of registering a first and a second 3D image computed respectively from the first and second set of 2D images so as to obtain a connected 3D image of the first and second portion of the region of interest. This embodiment can be implemented when the fiducials support in the first configuration is in proximity of the fiducials support in the second configuration such that the first and second portion of the region of interest in the first and second set of 2D images are at least partially overlapping. This embodiment may be notably implemented using the registration phantom having the longitudinal dimension of the elongated member as a multiple of the maximal distance between the projections of the distal and proximal fiducial on the longitudinal axis according to the embodiment described above. In this case, the same registration phantom may be first positioned in a first fixation position with the fiducials support spaced apart from the base and then positioned in a second fixation position with the fiducials support overlapping to the base. Due to the proportion of the elongated member with respect to the fiducials support, the first and second set of 2D images partially overlaps allowing the reconstruction of a connected 3D volume.

According to one embodiment, the receiving step is further configured to receive a third set of images of a third portion of the region of interest, said third set of images being obtained with a registration phantom fixed on the same base but in a different fixation position from the first and second fixation position. The third set of images is acquired in such a way that it comprises at least two 2D images containing each at least one detectable radiopaque fiducial of the registration phantom. According to this embodiment and if the third set of 2D images is partially overlapping with at least one of the first and/or second set of 2D images, the method may be further configured to reconstruct a connected 3D image from the registration of three set of 2D images.

According to one embodiment, the method comprises as well the preliminary step of providing an imaging kit and fixing the base to the skin or to a body part of the patient in proximity of the region of interest.

The method may comprise as well the step of mounting at least one registration phantom onto the base in a first fixation position using the base fixation element and phantom fixation element, wherein the position of the fiducials support in said first fixation position is known in a coordinate system of the base and acquiring with the X-ray imaging system at least one first set of 2D images of at least one first portion of the region of interest, wherein at least two 2D images contain each at least one detectable radiopaque fiducial of the registration phantom. Then the at least one registration phantom may be mounted onto the base in a second fixation position using the base fixation element and phantom fixation element, wherein the position of the fiducials support said second predetermined fixation position is known in the coordinate system of the base. Finally, at least one second set of 2D images of at least one second portion of the region of interest may be acquired with the X-ray imaging system, wherein at least two 2D images contain each at least one detectable radiopaque fiducial of the registration phantom.

The present invention further relates to computer program comprising instructions, which when the program is executed by a computer, causes the computer to carry out the steps of the method according to any one of the embodiments hereabove.

The computer program product to perform the method as described above may be written as computer programs, code segments, instructions or any combination thereof, for individually or collectively instructing or configuring the processor or computer to operate as a machine or special-purpose computer to perform the operations performed by hardware components. In one example, the computer program product includes machine code that is directly executed by a processor or a computer, such as machine code produced by a compiler. In another example, the computer program product includes higher-level code that is executed by a processor or a computer using an interpreter. Programmers of ordinary skill in the art can readily write the instructions or software based on the block diagrams and the flow charts illustrated in the drawings and the corresponding descriptions in the specification, which disclose algorithms for performing the operations of the method as described above.

The present invention also relates to computer-readable storage medium comprising instructions that when executed by a computer, causes the computer to carry out the steps of the method according to any one of the embodiments hereabove.

According to one embodiment, the computer-readable storage medium is a non-transitory computer-readable storage medium.

Computer programs implementing the method of the present embodiments can commonly be distributed to users on a distribution computer-readable storage medium such as, but not limited to, an SD card, an external storage device, a microchip, a flash memory device, a portable hard drive and software websites. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

The present invention further related to a data processing apparatus comprising a processor configured to perform the steps of the method according to any one of the embodiments described here above.

In one embodiment, the data processing apparatus comprises dedicated circuitry or a general-purpose computer, configured for receiving the acquired X-ray images and executing the steps of the method for registration of 2D images of at least one region of interest of a patient as described above. In one embodiment, the system comprises a processor and the computer program of the present invention.

In one embodiment, the system of the present invention comprises a communication module to transmit the 2D or 3D images or the anatomical points to a screen for visualization. The system may alternatively comprise an output module comprising a screen to display the registered images or a user interface.

BRIEF DESCRIPTION OF THE DRAWINGS

Features and advantages of the invention will become apparent from the following description of embodiments of a system, this description being given merely by way of example and with reference to the appended drawings in which.

ILLUSTRATIVE EMBODIMENTS OF THE INVENTION

Figure 1:
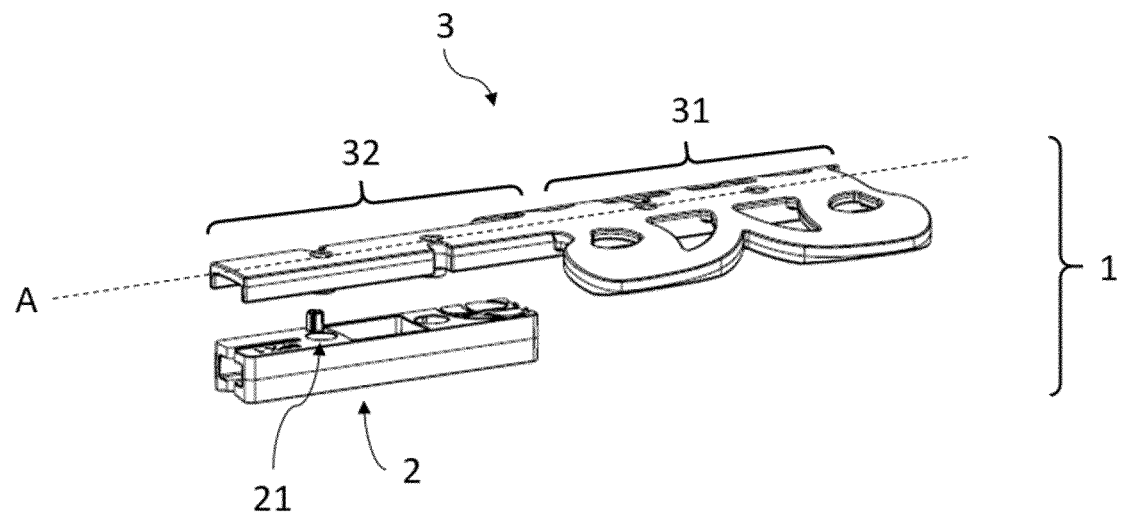
FIG. 1 is a perspective view of the base and the registration phantom according to a first embodiment of the invention.
Figure 2:
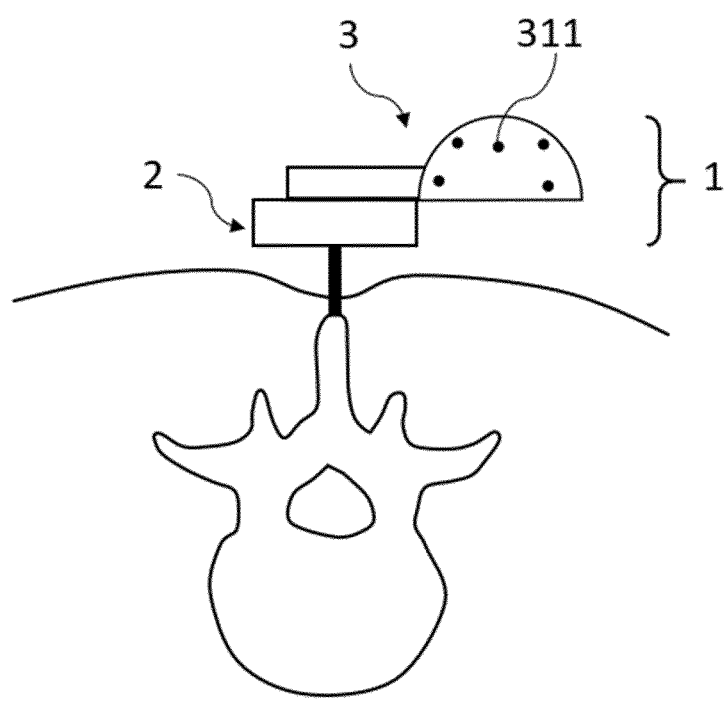
FIG. 2 schematically illustrates the base rigidly secured to a patient's bone while the registration phantom is fixed on the base according to a first embodiment of the invention.

According to a first embodiment of the invention illustrated in FIG. 1, the imaging kit 1 comprises a base 2 and a registration phantom 3. The base 2, made of a substantially radiotransparent material, is configured to be rigidly secured to a patient's bone, as shown in FIG. 2. The registration phantom 3 comprises a fiducials support 31 of substantially radiotransparent material comprising a plurality of radiopaque fiducials 311 disposed in a known 3D position in a coordinate system of said registration phantom 3. According to this first embodiment, the base 2 comprises a base fixation element 21 and the registration phantom 3 comprises a phantom fixation element for reproducibly attaching the registration phantom 3 to the base 2. The registration phantom 3 comprises an elongated member 32 extending from the fiducials support 31 along a longitudinal axis A. The elongated member 32 bears the phantom fixation element. The elongated member 32 and the base fixation element 21 and phantom fixation element are configured so as to provide at least one fixation position where the fiducials support 31 is spaced apart from the base 2, as shown in FIGS. 1 and 2, so as to extend over a different region of the patient's body from the region over which the base extends. In this first embodiment, the elongated member is directly fixed on the base and the elongated member fits the width and the length of the base.

Figure 3:
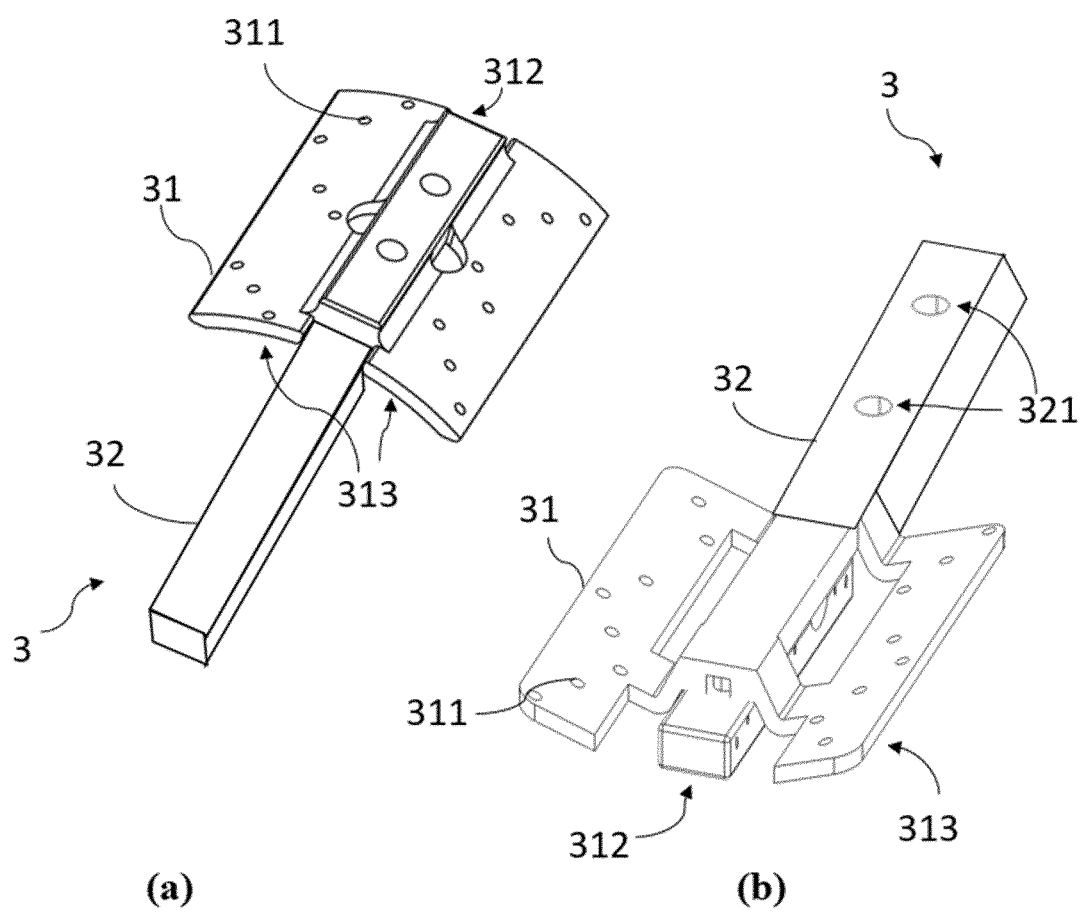
FIGS. 3a and 3b are a front and rear perspective view of one registration phantom.

FIGS. 3*a* and *b* shows two perspective views of the rear and the front of the registration phantom 3. As shown, the fiducials support 31 comprises a central portion 312 and two lateral wings 313 extending on either side of said central portion 312. In this embodiment, the wings 313 extends below the central portion 312 and have a curved surface. In this embodiment, the fiducial wings 313 comprise the radiopaque fiducials 311. FIG. 3*b* shows, according to the first embodiment, a configuration of the phantom fixation element 321 comprised in the elongated member 32.

Figure 4:
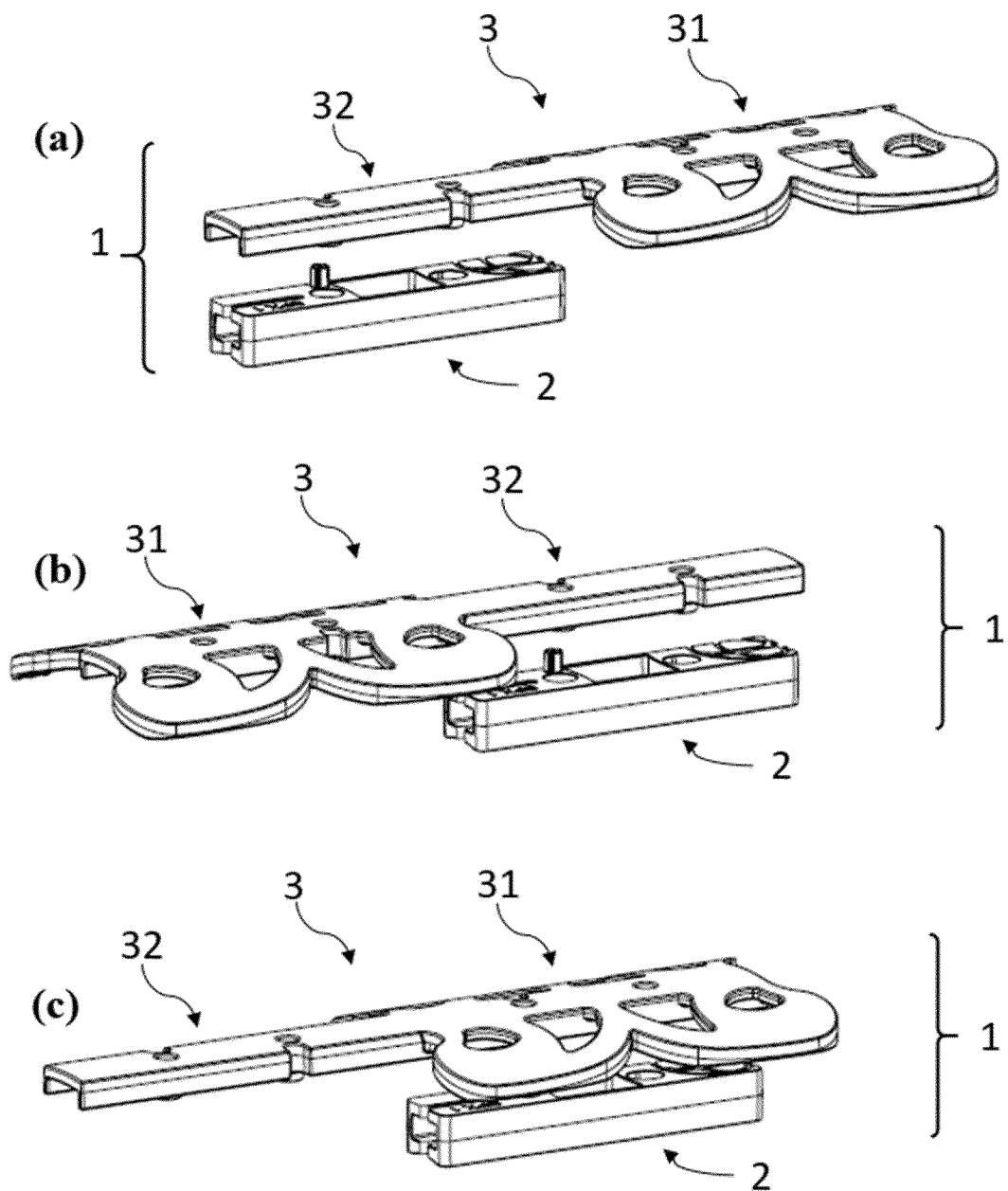
FIGS. 4a, 4b and 4c are perspective exploded views of the base and the registration phantom according to a second embodiment where the base fixation element and phantom fixation element are configured to provide multiple fixation positions of the registration phantom.

FIG. 4 shows some of the different fixation position of the imaging kit. According to a second embodiment of the invention shown by FIGS. 4*a* and 4*b*, the elongated member 32, the base fixation element 21 and phantom fixation element 321 are configured so as to provide at least two fixation positions where the fiducials support 31 is spaced apart from the base 2. In this illustrated embodiment, the base fixation element 21 comprises two openings positioned along the longitudinal axis A which are configured to receive and cooperate with two pins protruding from the elongated member 32. The registration phantom 3 may be than fixed to the base 2 in a first fixation position illustrated in FIG. 4*a* or in a symmetric second fixation position illustrated in FIG. 4*b*. In this case the same base fixation element 21 and phantom fixation element 321 allow to fix the registration phantom in both first and second fixation position. According to this second embodiment as illustrated in FIG. 4*c*, the registration phantom comprises a second phantom fixation element configured to ensure a third fixation position where the fiducials support 31 and the base 2 overlaps. In this second embodiment, the central portion 312 comprises the second phantom fixation element.

Figure 5:
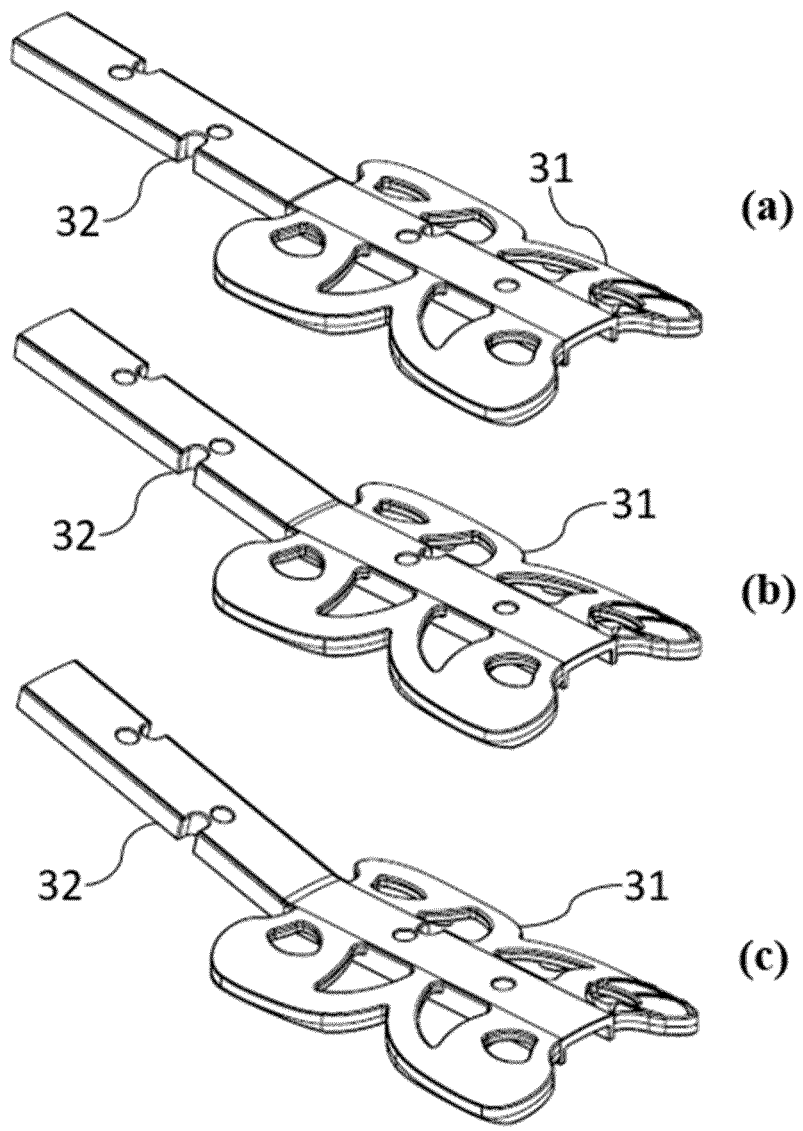
FIGS. 5*a*, 5*b* and 5*c* are perspective views of the registration phantom according to a third embodiment of the invention where the elongated member is tilted with respect to the plane on which lies the fiducials support.

According to a third embodiment illustrated in FIG. 5, the elongated member 32 and the central portion of the fiducials support 31 form an angle at the insertion point of the elongated member 32 into the fiducials support 31. FIGS. 5*a*, 5*b* and 5*c* illustrate different angles that may be formed between the elongated member 32 and the central portion of the fiducials support 31.

Figure 6:
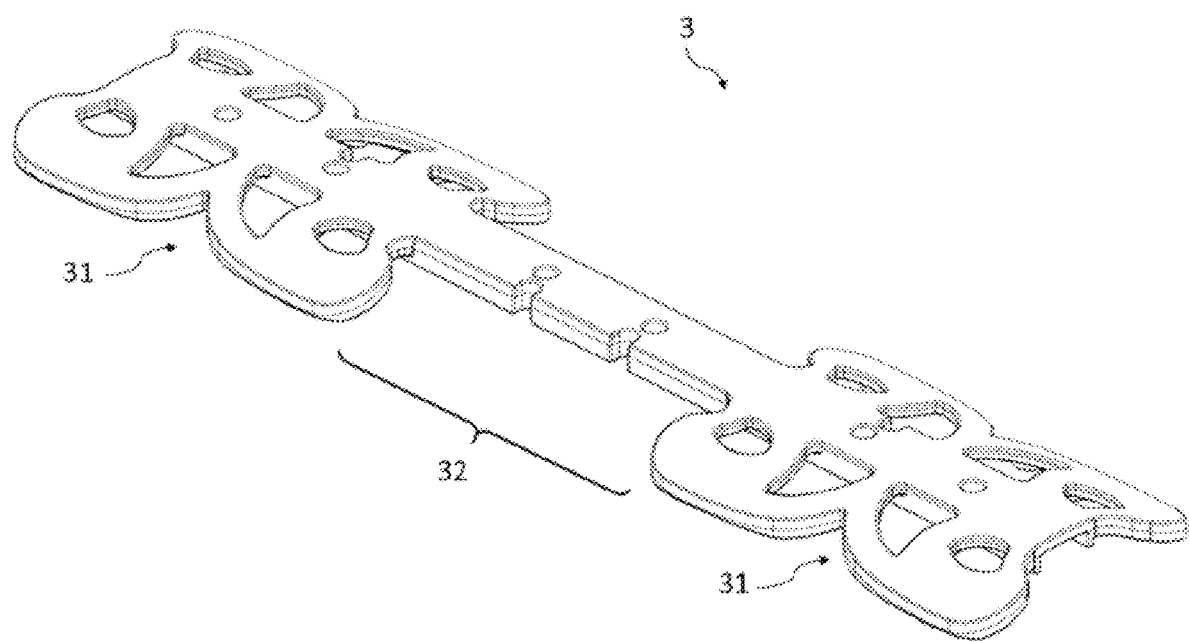
FIG. 6 is a perspective view of the registration phantom according to a fourth embodiment of the invention where the registration phantom comprises two fiducials support.

According to a fourth embodiment illustrated in FIG. 6, the registration phantom 3 comprises two fiducials supports 31 extending along the longitudinal axis A, one on each end of the elongated member 32. In this embodiment, the two fiducials support has the same shape and dimensions.

Figure 7:
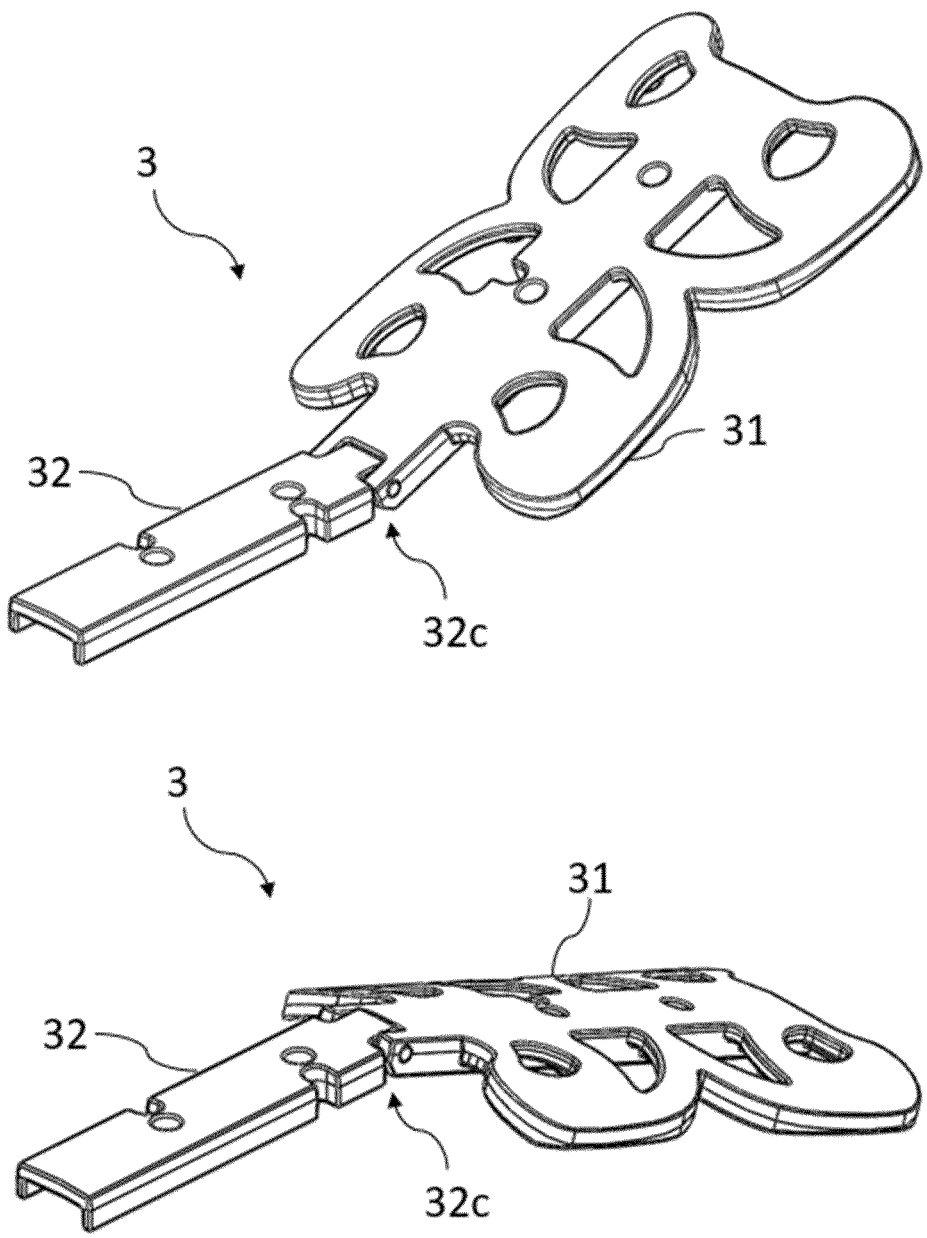
FIG. 7 is a perspective view of the registration phantom according to a fifth embodiment of the invention where the elongated member is serially movably connected to the fiducial support.

FIG. 7 illustrate a fifth embodiment of the invention where the elongated member 32 is serially movably connected to the fiducial support 31 by a hinger connection element 32*c*. FIG. 7 shows the registration phantom 3 in two possible configurations where the elongated member 32 is tilted with respect to the fiducial support 31 into two different angles.

Figure 8:
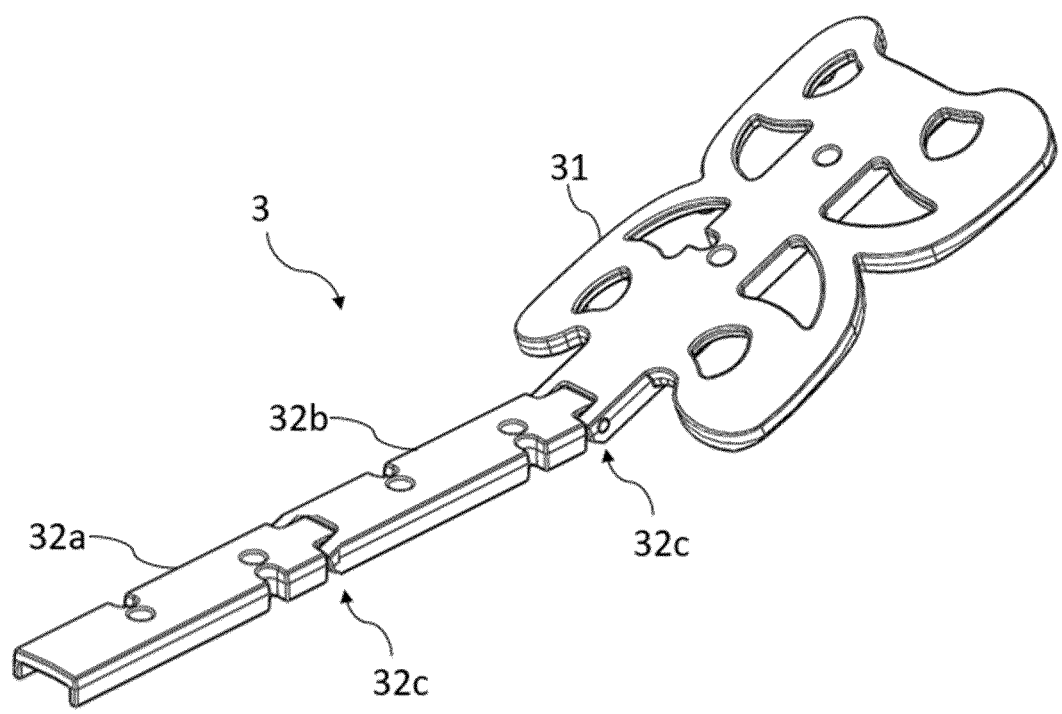
FIG. 8 is a perspective view of the registration phantom according to a sixth embodiment of the invention where the elongated member comprises at least two elements serially movably connected to each other.

FIG. 8 illustrate a sixth embodiment of the invention where the elongated member comprises a first element 32*a* and a second element 32*b* serially connected to each other's by a hinge connection 32c and where one end of the second element 32b is movably connected using a hinge connector 32c to the fiducial support 31.

Figure 9:
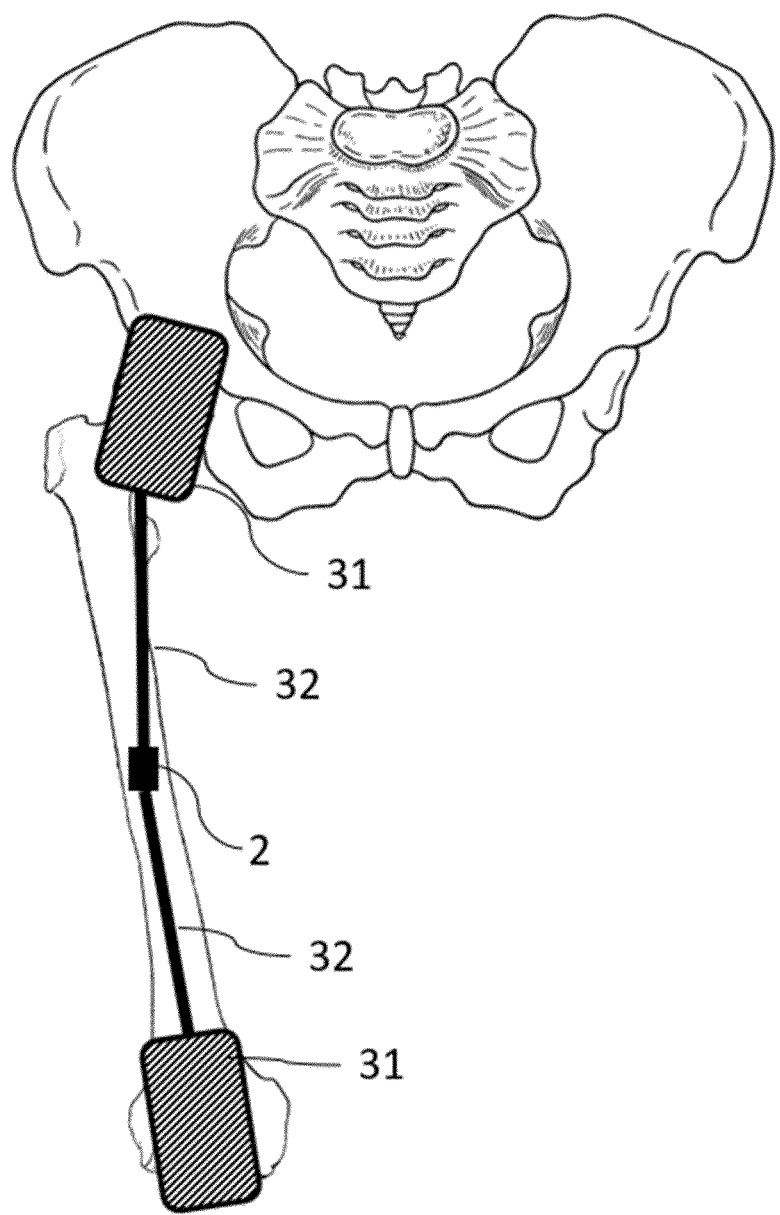
FIG. 9 is a schematic illustration of the imaging kit according to a seventh embodiment where the base is fixed on the femur and the two registration phantoms are fixed on the base so that one fiducials support extends over the kneecap and the other extends over the neck of the femur.

FIG. 9 illustrates a seventh embodiment where the imaging kit 1 comprises one base 2 and two registration phantoms 3. In this embodiment the base 2 is configured to be rigidly fixed on the femur and the first registration phantom 3 is configured to have its fiducials support 31 extending over the kneecap when the registration phantom 3 is attached to the base 2. In this configuration, a set of 2D images comprising at least two fiducials of the first registration phantom 3 allows the registration of 2D images or 3D image of the kneecap. The one second registration phantom 3 is configured to have its fiducials support 31 extending over the neck of the femur when the registration phantom 3 is attached to the base fixed on the femur 2. In this configuration, a set of 2D images comprising at least two fiducials of the second registration phantom 3 allows the registration of 2D images or 3D image of the neck of the femur. Using the method of the present invention, the registered images of the neck of the femur and kneecap can be registered in the coordinate system of the base 2.

Figure 10:
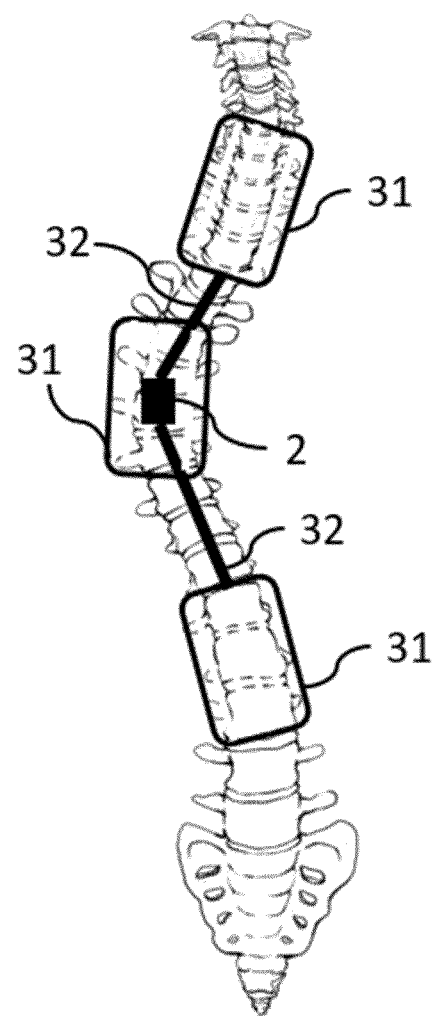
FIG. 10 is a schematic illustration of the imaging kit according to an eighth embodiment where the base is fixed on vertebra and three registration phantoms are disposed along the spine. The fiducials supports are shown in transparence to better illustrate their positioning with respect the different portions of the spine.

FIG. 10 illustrates an eighth embodiment wherein the imaging kit is configured to allow the registration of 2D or 3D images of three portions of the spine of a subject in the coordinate system of the base 2. In this embodiment, the imaging kit 1 comprises one base 2, configured to be rigidly fixed on at least one vertebra of the patient, notably on the spinous process of the vertebra, and three registration phantoms 3. In this embodiment, the first registration phantom 3 is fixed to the base 2 using the phantom second fixation element so that the fiducials support 31 overlaps to the base 2. The second and the third registration phantom 3 are fixed to the base 2 through their respective elongated members 31 so that the second and third fiducials support 31 are positioned along the spine of the subject in two positions spaced apart from the base 2.

Figure 11:
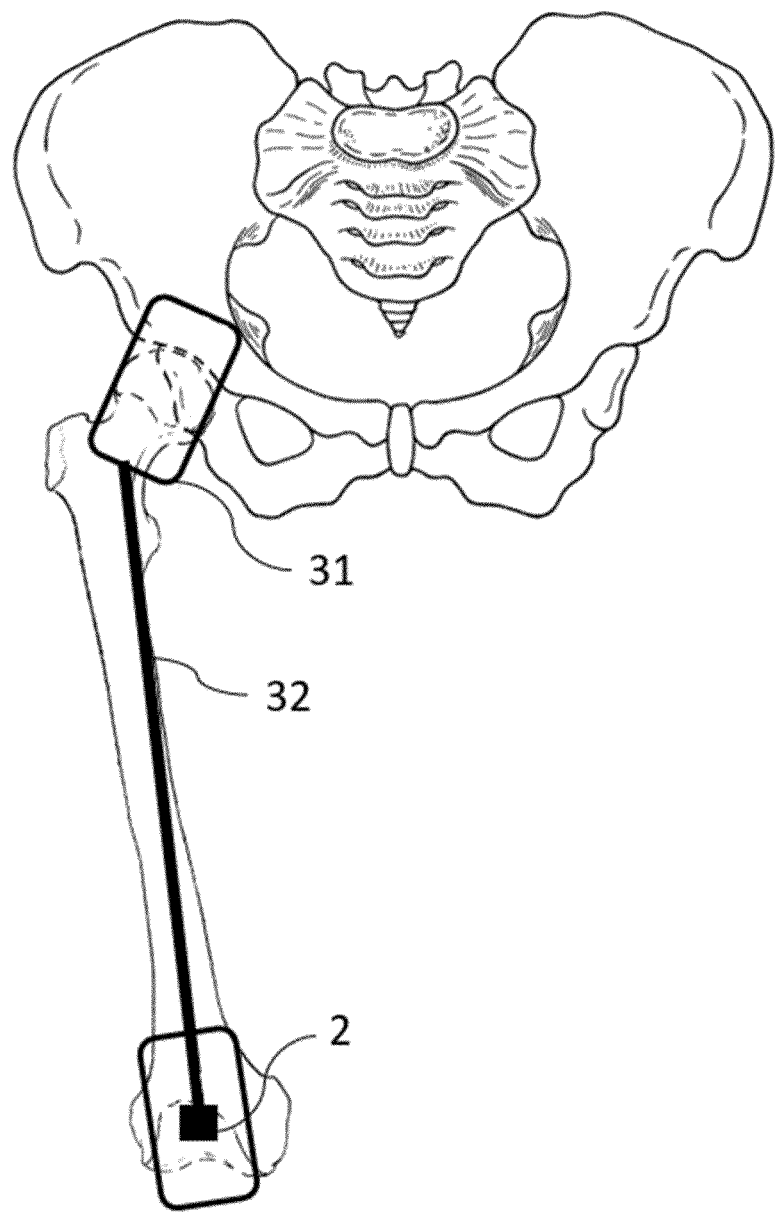
FIG. 11 is a schematic illustration of the imaging kit according to a ninth embodiment where the base is fixed on knee and the registration phantom is fixed on the base so that fiducial support extends over the hip center.

FIG. 11 illustrates a ninth embodiment of the imaging kit, where the base is configured to be fixed on the knee and the registration phantom is configured so that when it is fixed on the base, the fiducial support extends over the hip center.

Figure 12:
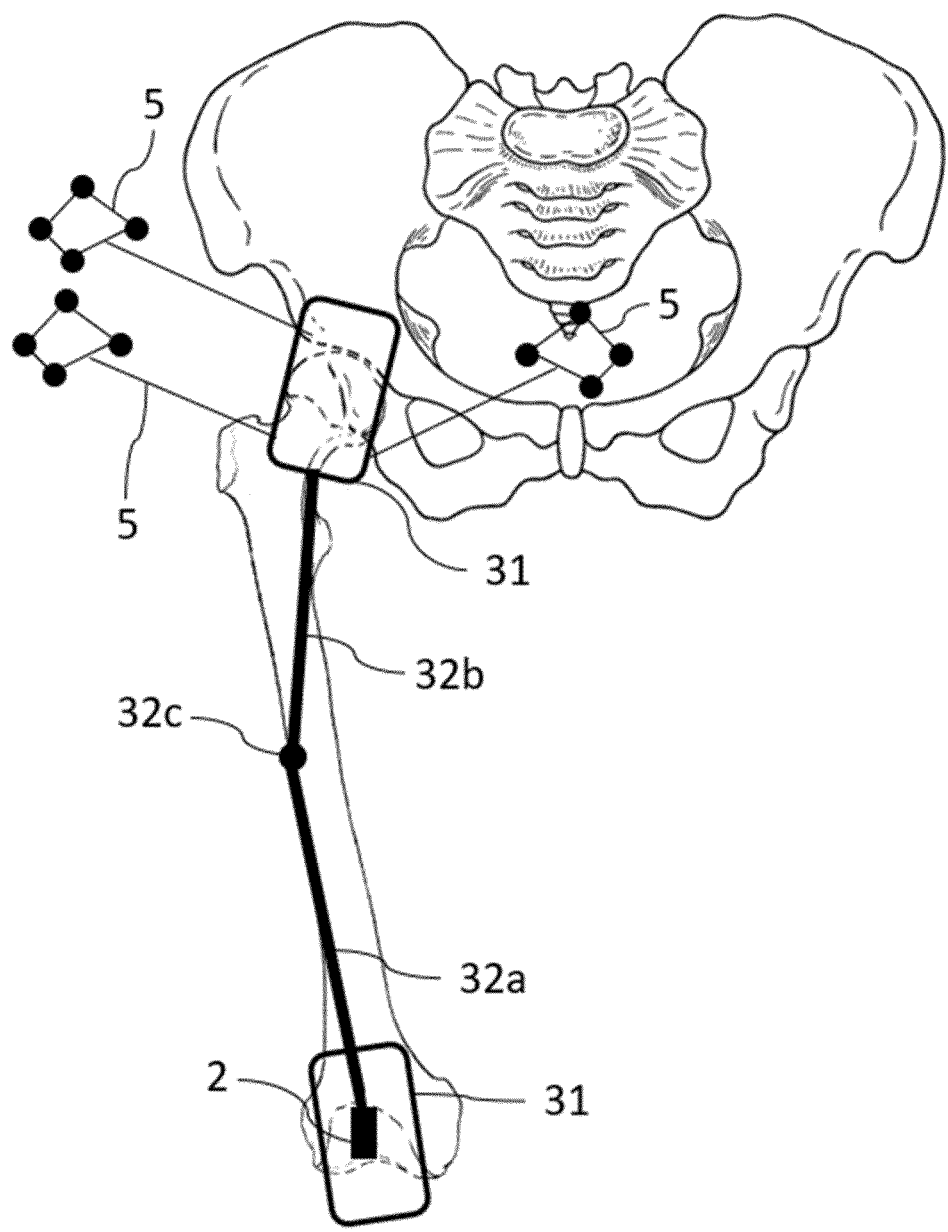
FIG. 12 is a schematic illustration of the imaging kit according to a tenth embodiment where the base is fixed on knee and an articulated registration phantom is fixed on the base so that fiducial support extends over the hip center.

FIG. 12 illustrates a tenth embodiment where an articulated registration phantom comprising a first 32a and a second 32b element of the elongated member tilted thanks to the connection element 32c. In this embodiment the base is fixed to the knee and the first 32a and second 32b element are tilted so that when the registration phantom is fixed on the base the fiducial support extends over the hip center. In this embodiment three tracker elements 5 are fixed on the fiducial support on the hip center in order to precisely detect its relative position so as to determine the position of the fiducials in the coordinated system of the base.

Figure 13:
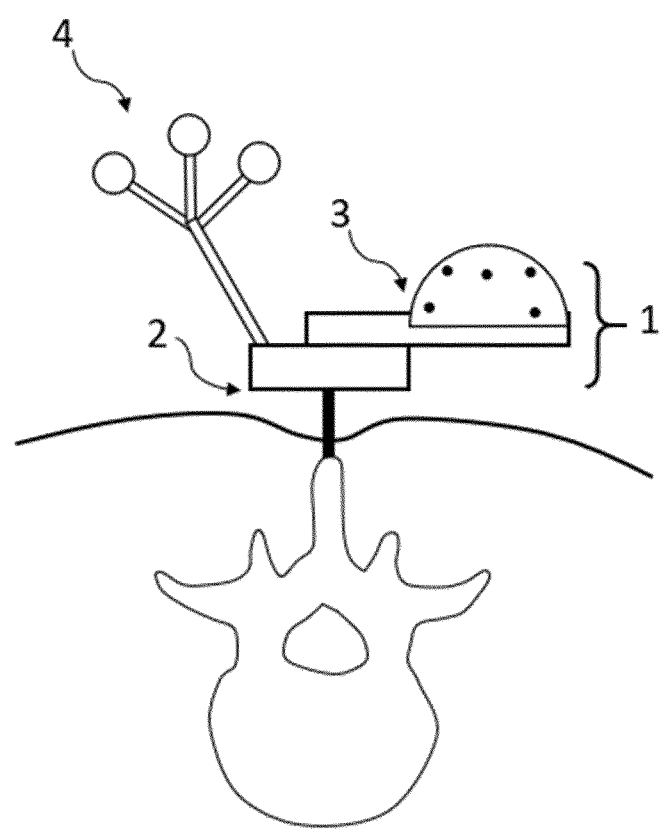
FIG. 13 is a schematic illustration of the imaging kit where the base is rigidly secured to a patient's bone and both the tracker and the registration phantom are fixed on the base according to a ninth embodiment.

In the embodiment illustrated in FIG. 13, the tracker 4 is an optical tracker comprising a plurality of reflective balls having a known relative position.

Figure 14:
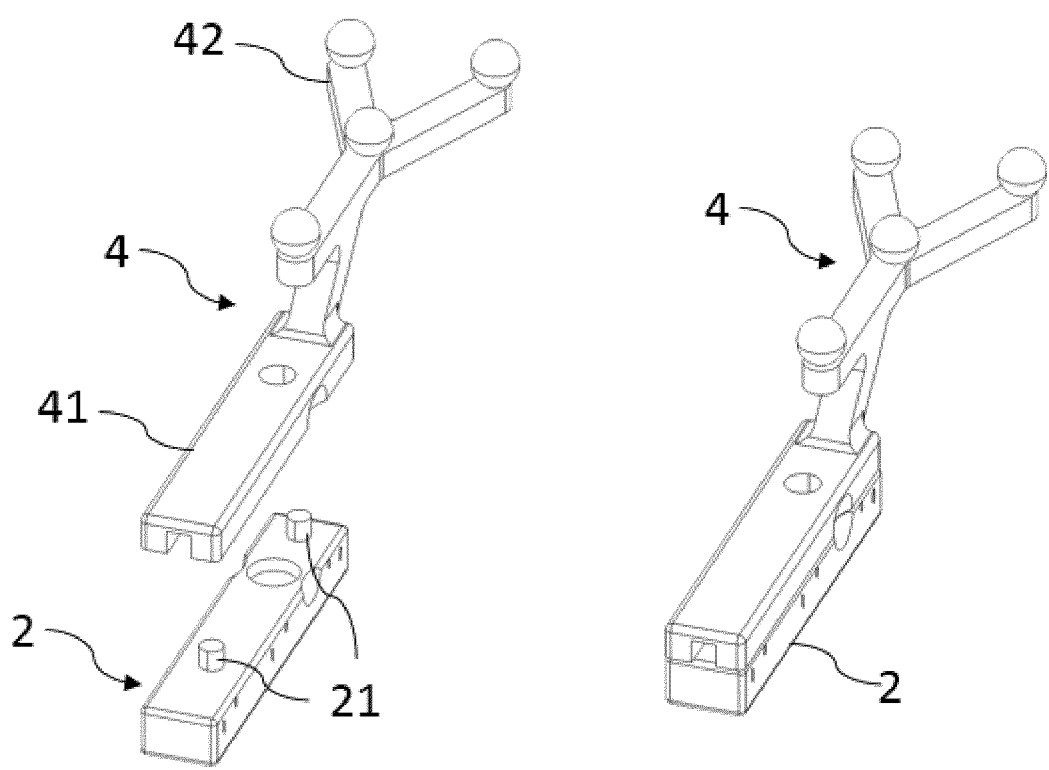
FIG. 14 are perspective exploded views of the base and the tracker of an imaging kit according to one embodiment of the invention.

According to this embodiment, the tracker 4 can be removably fixed to the base 2 by a reproducible fixation that allows one or more determined possible positions of the tracker with respect to the base. For example, the tracker 4 comprises a support 41 comprising two cylindrical protrusions engaging respective cylindrical openings 21 in the surface opposite to the support surface of the base 2. The tracker 4 comprises a reference point to determine the real position of the tracker 4 relative to the base 2 using a tracked tool 42. As the base fixation elements 21 and tracker fixation elements are disposed along the longitudinal axis of the base, the tracker 4 can be attached in two fixation positions so that the tracked tool 42 can be placed on the distal end of the base (as shown in FIG. 14) or on the proximal end of the base.

Such a symmetric fixation is advantageous in that it provides more flexibility to the medical staff to position the tracker in the operating space, in particular depending on the position of a localization camera that is used for navigation. It is also advantageous to release the constraint linked to positioning of the base onto the bone at the beginning of the surgical procedure; the medical staff can focus on positioning of the base relative to the bone choosing positioning direction depending only on bone quality of bone fixation and afterwards position the tracker onto base depending on the suitable operating set-up. However, there may be more than two possible positions for the tracker. For example, for a base having a substantially circular shape (not shown), the base fixation element could comprise a conical protrusion in the center of the base and pins arranged at given angular positions to define the possible positions of the tracker.

Figure 15:
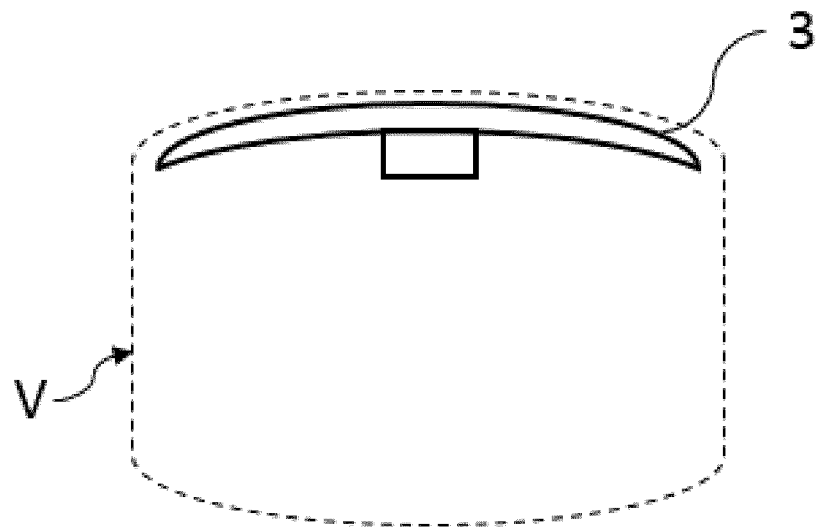
FIG. 15 is a representation of the volume that can be reconstructed by a 3D image for a given position of the registration phantom which is schematically illustrated as the cross sections in the horizontal plane of the fiducials support and the volume reconstructed in the 3D image.

FIG. 15 shows the volume V that may be registered in one 3D image using the method of the present invention for a given position of the registration phantom 3. The Figure shows the cross sections in the horizontal plane of the registration phantom 3 and the volume V reconstructed in the 3D image.

Figure 16:
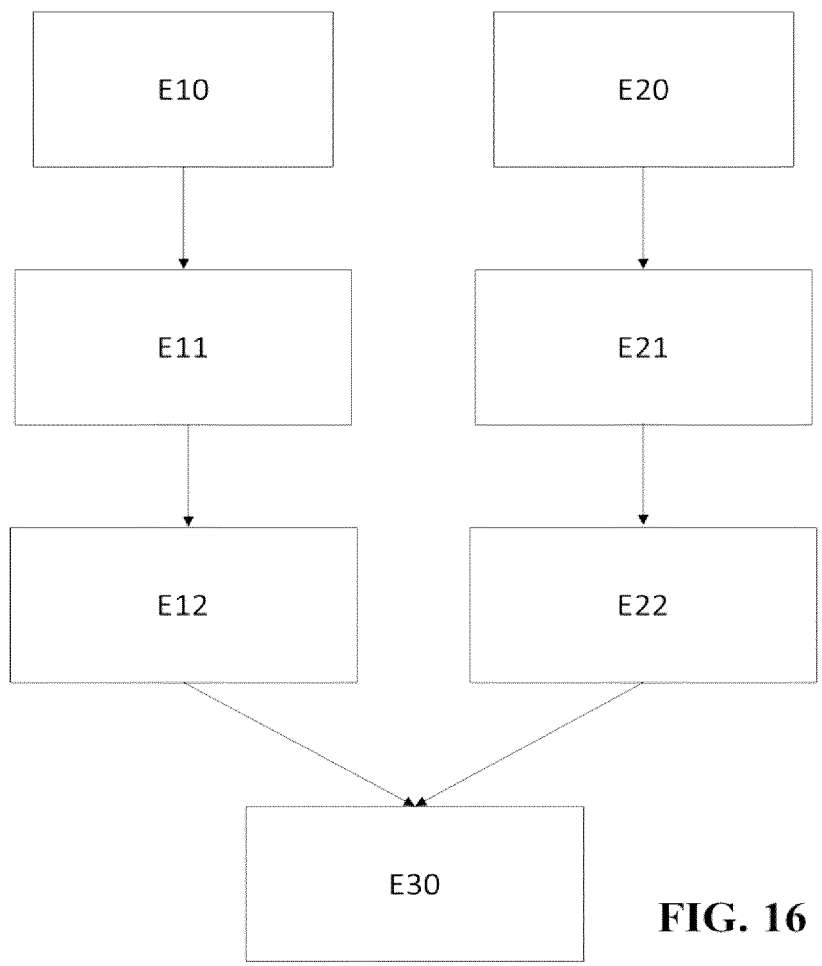
FIG. 16 is a block diagram illustrating a method for registration of 2D images of at least one region of interest of a patient according to an embodiment of the invention.

FIG. 16 is a block diagram illustrating a method for registration of 2D images of at least one region of interest of a patient according to an embodiment of the invention.

The method, as illustrated by way of example in FIG. 16, may comprise the step E10 of placing the elongated member 32, the at least one base fixation element 21 and the at least one phantom fixation element 321 in a first fixation position. In said first fixation position, the fiducial support 31 may be substantially positioned facing the base 2, and the registration phantom 3 may be positioned in the phantom first fixation position. The registration phantom 3 in the phantom first fixation position may extend substantially over a first region of the patient's body. Then, the first set of 2D X-ray images of the at least one first portion of the region of interest is acquired and received in step E11.

After acquisition of the first set of 2D X-ray images, the elongated member 32, the method may comprise the step E20 of placing the at least one base fixation element 21 and the at least one phantom fixation element 321 in a second fixation position different, that is to say spaced apart from, from the phantom first fixation position. In said second fixation position, the fiducials support 31 may be spaced apart from the base 2 such that the fiducials support 31 extends over a second region of the patient's body distant from the first region, and the registration phantom 3 may be positioned in the phantom second fixation position. The registration phantom 3 in the phantom second fixation position may extend substantially over the second region of the patient's body, the second region of the patient's body being distant from the first region. Then, the second set of 2D X-ray images of the at least one second portion of the region of interest is acquired and received in step E21.

The method further comprises the step E12 of registering the first set of images in the coordinate system of the registration phantom in the first phantom fixation position and the step E22 of registering the second set of images in the coordinate system of the registration phantom in the second phantom fixation position.

The method further comprises the step E30 of registering the first and second sets of 2D images in the coordinate system of the base using the known position of the fiducials support 31 in the coordinate system of the base 2 for the first and second phantom fixation positions.

The first and second fixation positions may be chosen such that the acquired first portion of the region of interest in the first set of 2D images is separated and disconnected from the acquired second portion of the region of interest in the second set of 2D images, that is to say that the acquired first and second portions of the region of interest are not overlapping. Thus, two separate and disconnected volumes of the region of interest are acquired.

Alternatively, the first fixation position and the second fixation position may be chosen such that the acquired first and second portions of the region of interest in the first and second sets of 2D images are at least partially overlapping. Thus, a connected 3D image of the first and second portions of the region of interest may be obtained.

The invention claimed is:

1. A method for registration of 2 dimensional (2D) images of at least one region of interest of a patient, wherein the images are acquired using an X-ray imaging system and an imaging kit, said imaging kit comprising:
   a base, made of a substantially radiotransparent material, said base being configured to be rigidly secured to a patient's bone over a first region of a patient's body; and
   at least one registration phantom having a fiducials support of substantially radiotransparent material comprising a plurality of radiopaque fiducials;
the base comprising at least one base fixation element and the at least one registration phantom comprising at least one phantom fixation element for reproducibly attaching the registration phantom to the base;
wherein the at least one registration phantom comprises at least one elongated member bearing the at least one phantom fixation element and extending from the fiducials support, and wherein the elongated member, the at least one base fixation element and the at least one phantom fixation element are configured so as to provide at least one fixation position where the fiducials support is spaced apart from the base such that the fiducials support extends over a second region of the patient's body distant from the first region, wherein the method comprises the following steps:
   receiving at least one first set of 2D X-ray images of at least one first portion of the region of interest and a second set of 2D X-ray images of at least one second portion of the region of interest, wherein the base is fixed on a skin or a body part of the patient and the registration phantom is attached to the base in a first phantom fixation position during the acquisition of the first set of 2D X-ray images and the registration phantom is attached to the base in a second phantom fixation position different from the first phantom fixation position during the acquisition of the second set of 2D X-ray images, such that said first and second sets of images comprise each at least two 2D images containing each at least one detectable radiopaque fiducial of the registration phantom; wherein a position of the fiducials support in a coordinate system of the base in the first and second phantom fixation positions is known;
   registering the first set of images in the coordinate system of the registration phantom in the first phantom fixation position and the second set of images in the coordinate system of the registration phantom in the second phantom fixation position; and
   registering the first and second sets of 2D images in the coordinate system of the base using the known position of the fiducials support in the coordinate system of the base for the first and second phantom fixation positions.

2. The method according to claim 1, further comprising a step of computing at least one 3D image within the coordinate system of the base using at least a part of the first and/or second set of 2D images.

3. The method according to claim 1, wherein at least two 2D images of the first or second set of 2D images are used to determine a position of at least one anatomical point in the coordinate system of the base.

4. The method according to claim 1, wherein the first fixation position and the second fixation position are chosen such that the first and second portions of the region of interest in the first and second sets of 2D images are at least partially overlapping; and the method further comprises a step of registering a first and a second 3D image computed respectively from the first and the second set of 2D images so as to obtain a connected 3D image of the first and second portions of the region of interest.

5. The method according to claim 1, wherein the imaging kit further comprises a tracker comprising a tracker fixation element configured to reproducibly rigidly attach the tracker to the base, wherein the base fixation element is configured to reproducibly interchangeably attach the tracker and the registration phantom.

6. The method according to claim 1, wherein the tracker is an optical tracker, an ultrasound-based tracker or an electromagnetic tracker.

7. The method according to claim 1, wherein the fiducials in the fiducials support are disposed on a curved surface having a predefined curvature radius.

8. The method according to claim 1, wherein the elongated member extends from the fiducials support along a longitudinal axis and a 3D position of the plurality of radiopaque fiducials is known in a coordinate system of said registration phantom.

9. The method according to claim 1, wherein the elongated member comprises at least two elements serially movably connected to each other.

10. The method according to claim 1, wherein the imaging kit comprises at least first and second registration phantoms wherein the first registration phantom and the second registration phantom comprise cooperating fixation elements configured to attach the first registration phantom to the second registration phantom while being reproducibly fixed to the base.

11. The method according to claim 1, wherein the base fixation element and phantom fixation element comprise complementary magnetic elements configured to maintain the base and the registration phantom attached to each other.

12. The method according to claim 1, wherein the base is rigidly fixed on at least one vertebra of the patient, notably on a spinous process of the vertebra.

13. The method according to claim 1, wherein the base is rigidly fixed on a femur of the patient and the fiducials support of a first registration phantom attached to the base extends over a kneecap of the patient.

14. The method according to claim 13, wherein the fiducials support of a second registration phantom attached to the base extends over a neck of the femur.

15. The method according to claim 1, wherein the base is rigidly fixed on the tibia of the patient and the fiducials support of the at least one registration phantom attached to the base extend over a calcaneus of the patient.

16. A system for registration of 2 dimensional (2D) images of at least one region of interest of a patient, comprising:

(i) an X-ray imaging system adapted to acquire said 2D X-ray images,
(ii) an imaging kit comprising:
a base made of a substantially radiotransparent material, said base (2) being configured to be rigidly secured to a patient's bone over a first region of a patient's body; and
at least one registration phantom having a fiducials support of substantially radiotransparent material comprising a plurality of radiopaque fiducials;
the base comprising at least one base fixation element and the at least one registration phantom comprising at least one phantom fixation element for reproducibly attaching the registration phantom to the base;
wherein the at least one registration phantom comprises at least one elongated member bearing the at least one phantom fixation element and extending from the fiducials support, and wherein the elongated member, the at least one base fixation element and the at least one phantom fixation element are configured so as to provide at least one fixation position where the fiducials support is spaced apart from the base such that the fiducials support extends over a second region of the patient's body distant from the first region,
(iii) a control unit configured to:
receive at least one first set of 2D X-ray images of at least one first portion of the region of interest and a second set of 2D X-ray images of at least one second portion of the region of interest, wherein the base is fixed on the skin or a body part of the patient and the registration phantom is attached to the base in a first phantom fixation position during the acquisition of the first set of 2D X-ray images and the registration phantom is attached to the base in a second phantom fixation position different from the first phantom fixation position during the acquisition of the second set of 2D X-ray images, such that said first and second sets of images comprise each at least two 2D images containing each at least one detectable radiopaque fiducial of the registration phantom; wherein a position of the fiducials support in a coordinate system of the base in the first and second phantom fixation positions is known;
register the first set of images in the coordinate system of the registration phantom in the first phantom fixation position and the second set of images in the coordinate system of the registration phantom in the second phantom fixation position; and
register the first and second sets of 2D images in the coordinate system of the base using the known position of the fiducials support in the coordinate system of the base for the first and second phantom fixation positions.

17. The system according to claim 16, wherein the control unit is further configured to compute at least one 3D image within the coordinate system of the base using at least a part of the first and/or second set of 2D images.

18. The system according to claim 16, wherein the control unit is configured to use at least two 2D images of the first or second set of 2D images to determine the position of at least one anatomical point in the coordinate system of the base (2).

19. The system according to claim 16, wherein the control unit is further configured, when the first fixation position and the second fixation position are chosen such that the first and second portions of the region of interest in the first and second sets of 2D images are at least partially overlapping, to register a first and a second 3D image computed respectively from the first and the second set of 2D images so as to obtain a connected 3D image of the first and second portions of the region of interest.

20. The system according to claim 16, wherein the imaging kit further comprises a tracker comprising a tracker fixation element configured to reproducibly rigidly attach the tracker to the base, wherein the base fixation element is configured to reproducibly interchangeably attach the tracker and the registration phantom.

21. The system according to claim 20, wherein the tracker is an optical tracker, an ultrasound-based tracker or an electromagnetic tracker.

22. The system according to claim 16, wherein the fiducials in the fiducials support are disposed on a curved surface having a predefined curvature radius.

23. The system according to claim 16, wherein the elongated member extends from the fiducials support along a longitudinal axis and a 3D position of the plurality of radiopaque fiducials is known in a coordinate system of said registration phantom.

24. The system according to claim 16, wherein the elongated member comprises at least two elements serially movably connected to each other.

25. The system according to claim 16, wherein the imaging kit comprises at least first and second registration phantoms wherein the first registration phantom and the second registration phantom comprise cooperating fixation elements configured to attach the first registration phantom to the second registration phantom while being reproducibly fixed to the base.

26. The system according to claim 16, wherein the base fixation element and phantom fixation element comprise complementary magnetic elements configured to maintain the base and the registration phantom attached to each other.

* * * * *